United States Patent [19]
Lustig et al.

[11] Patent Number: 5,866,098
[45] Date of Patent: *Feb. 2, 1999

[54] ASSAY FOR IDENTIFYING EXTRACELLULAR SIGNALING PROTEINS

[75] Inventors: Kevin D. Lustig, Cambridge; Marc W. Kirschner, Newton, both of Mass.

[73] Assignee: President and Fellows of Harvard College, Cambridge, Mass.

[*] Notice: The term of this patent shall not extend beyond the expiration date of Pat. No. 5,585,087.

[21] Appl. No.: 764,179

[22] Filed: Dec. 13, 1996

Related U.S. Application Data

[63] Continuation of Ser. No. 255,677, Jun. 8, 1994, Pat. No. 5,585,087.

[51] Int. Cl.[6] .................................................. A61K 49/00
[52] U.S. Cl. ........................... 424/9.2; 424/9.1; 424/93.1; 424/93.2; 435/320.1; 435/69.1; 435/4; 435/6; 435/7.21; 435/7.4; 435/455; 435/325
[58] Field of Search .............................. 435/320.1, 69.1, 435/4, 6, 7.21, 7.4, 455, 325; 424/93.1, 9.2, 9.1, 93.2; 935/66, 70, 76

[56] References Cited

U.S. PATENT DOCUMENTS 5,075,227  12/1991  Hagen ................................. 435/91.41
5,585,087  12/1996  Lustig et al. ............................ 424/9.2

OTHER PUBLICATIONS

Watson et al. 1987 in: Molecular Biology of the Gene, Fourth Edition, Benjamin/Cummings Publishing Co., Menlo park, CA, p. 313.

Patten et al. 1974 in:Foundations of Embryology, Third Edition, McGraw–Hill Book Company, New York, NY, pp., 22, 24, 25, 342, 349–350.

Jessell et al. 1992, Cell 68: 257–270.

Pederson (ed.) 1994, in: Current Topics in Developmental Biology, vol. 29, Academic Press, San Diego, CA, p. 156.

*Primary Examiner*—Christopher S. F. Low
*Attorney, Agent, or Firm*—Matthew P. Vincent; Beth E. Arnold; Foley, Hoag & Eliot LLP

[57] ABSTRACT

The present invention concerns a novel paracrine signaling assay.

8 Claims, 2 Drawing Sheets

|  | 1 | 2 | 3 | 4 | 5 | 6 | 7 | 8 | 9 | 10 |
|---|---|---|---|---|---|---|---|---|---|---|
| 10 | 10 | 30 | | | | | | | | 100 |
| 9 | 9 | 29 | | | | | | | | 99 |
| 8 | 8 | 28 | | | | | | | | 98 |
| 7 | 7 | 27 | | | | | | | | 97 |
| 6 | 6 | 26 | | | | | | | | 96 |
| 5 | 5 | 25 | ⋮ | | | | | | | 95 |
| 4 | 4 | 24 | 34 | | | | | | | ⋮ |
| 3 | 3 | 23 | 33 | | | | | | | |
| 2 | 2 | 22 | 32 | | | | | | | |
| 1 | 1 | 21 | 31 | | | | | | | |

POOL ROWS (vertical axis) / POOL COLUMNS (horizontal axis)

*FIG. 2*

ASSAY FOR IDENTIFYING EXTRACELLULAR SIGNALING PROTEINS

This application is a continuation application of Ser. No. 08/255,677 filed on Jun. 8, 1994, now U.S. Pat. No. 5,585, 087. The contents of the aforementioned application is hereby incorporated by reference.

FUNDING

Work described herein was supported by finding from the National Institutes of Health. The United States Government has certain rights in the invention.

BACKGROUND OF THE INVENTION

Many types of communication take place among animal cells. These vary from long-range effects, such as those of rather stable hormones circulating in the blood and acting on any cells in the body that possess the appropriate receptors, however distant they are, to the fleeting effects of very unstable neurotransmitters operating over distances of only a few microns. Of particular importance in development is the class of cell interactions called embryonic induction; this includes influences operating between adjacent cells or in some cases over greater than 10 cell diameters (Saxen et al. (1989) *Int J Dev Biol* 33:21–48; and Gurdon et al. (1987) *Development* 99:285–306). Embryonic induction is defined as in interaction between one (inducing) and another (responding) tissue or cell, as a result of which the responding cells undergo a change in the direction of differentiation. This interaction is often considered one of the most important mechanism in vertebrate development leading to differences between cells and to the organization of cells into tissues and organs. Adult organs in vertebrates, and probably in invertebrates, are formed through an interaction between epithelial and mesenchymal cells, that is, between ectoderm/endoderm and mesoderm, respectively.

The effects of developmental cell interactions are varied. Typically, responding cells are diverted from one route of cell differentiation to another, by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185–199).

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diversive cell types during tissue differentiation (Davidson, E., (1990) *Development* 108:365–389; Gurdon, J. B., (1992) *Cell* 68:185–199; Jessell, T. M. et al., (1992) *Cell* 68:257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185–199).

The origin of the nervous system in all vertebrates, for example, can be traced to the end of gastrulation. At this time, the ectoderm in the dorsal side of the embryo changes its fate from epidermal to neural. The newly formed neuroectoderm thickens to form a flattened structure called the neural plate which is characterized, in some vertebrates, by a central groove (neural groove) and thickened lateral edges (neural folds). At its early stages of differentiation, the neural plate already exhibits signs of regional differentiation along its anterior posterior (A-P) and mediolateral axis (M-L). The neural folds eventually fuse at the dorsal midline to form the neural tube which will differentiate into brain at its anterior end and spinal cord at its posterior end. Closure of the neural tube creates dorsal/ventral differences by virtue of previous mediolateral differentiation. Thus, at the end of neurulation, the neural tube has a clear anterior-posterior (A-P), dorsal ventral (D-V) and mediolateral (M-L) polarities (see, for example, *Principles in Neural Science* (3rd), eds. Kandel, Schwartz and Jessell, Elsevier Science Publishing Company: NY, 1991; and *Developmental Biology* (3rd), ed. S. F. Gilbert, Sinauer Associates: Sunderland Mass., 1991). Inductive interactions that define the fate of cells within the neural tube establish the initial pattern of the embryonic vertebrate nervous system. In the spinal cord, the identify of cell types is controlled, in part, by signals from two midline cell groups, the notochord and floor plate, that induce neural plate cells to differentiate into floor plate, motor neurons, and other ventral neuronal types (van Straaten et al. (1988) *Anat. Embryol.* 177:317–324; Placzek et al. (1993) *Development* 117:205–218; Yamada et al. (1991) *Cell* 64:035–647; and Hatta et al. (1991) *Nature* 350:339–341). In addition, signals from the floor plate are responsible for the orientation and direction of commissural neuron outgrowth (Placzek, M. et al., (1990) *Development* 110:19–30). Besides patterning the neural tube, the notochord and floorplate are also responsible for producing signals which control the patterning of the somites by inhibiting differentiation of dorsal somite derivatives in the ventral regions (Brand-Saberi, B. et al., (1993) *Anat. Embryol.* 188:239–245; Porquie, O. et al., (1993) *Proc. Natl. Acad. Sci. USA* 90:5242–5246).

Another important signaling center exists in the posterior mesechyme of developing limb buds, called the Zone of Polarizing Activity, or "ZPA". When tissue from the posterior region of the limb bud is grafted to the anterior border of a second limb bud, the resultant limb will develop with additional digits in a mirror-image sequence along the anteroposterior axis (Saunders and Gasseling, (1968) *Epithelial-Mesenchymal Interaction*, pp. 78–97). This finding has led to the model that the ZPA is responsible for normal anteroposterior patterning in the limb. The ZPA has been hypothesized to function by releasing a signal, termed a "morphogen", which forms a gradient across the early embryonic bud. According to this model, the fate of cells at different distances from the ZPA is determined by the local concentration of the morphogen, with specific thresholds of the morphogen inducing successive structures (Wolpert, (1969) *Theor. Biol.* 25:1–47). This is supported by the finding that the extent of digit duplication is proportional to the number of implanted ZPA cells (Tickle, (1981) *Nature* 254:199–202).

SUMMARY OF THE INVENTION

The present invention concerns a novel paracrine signaling assay in which a "responsive" tissue is grafted onto an oocyte, or early stage embryo, which expresses exogenous proteins. Using the subject assay, it is possible to cause the oocyte to ectopically express secreted proteins, e.g. recombinant proteins, and then score for the effect of that protein on the grafted tissue, such as by detecting gene expression in the graft which is dependent on expression of the recombinant proteins by the oocyte. The subject assay will permit the identification of a variety of protein factors which are themselves active as inducing agents, or which act to antagonize an inducing agent, or which act to modify the response of the target tissue to an inducing agent. For instance, the subject assay can be employed to identify a vast number of protein factors which are regulators of cell proliferation, differentiation, or various other cell functions.

BRIEF DESCRIPTION OF THE FIGURE

FIG. 2 illustrates a 2-dimensional array for determining the pooling of test genes.

DETAILED DESCRIPTION OF THE INVENTION

Figure 1:
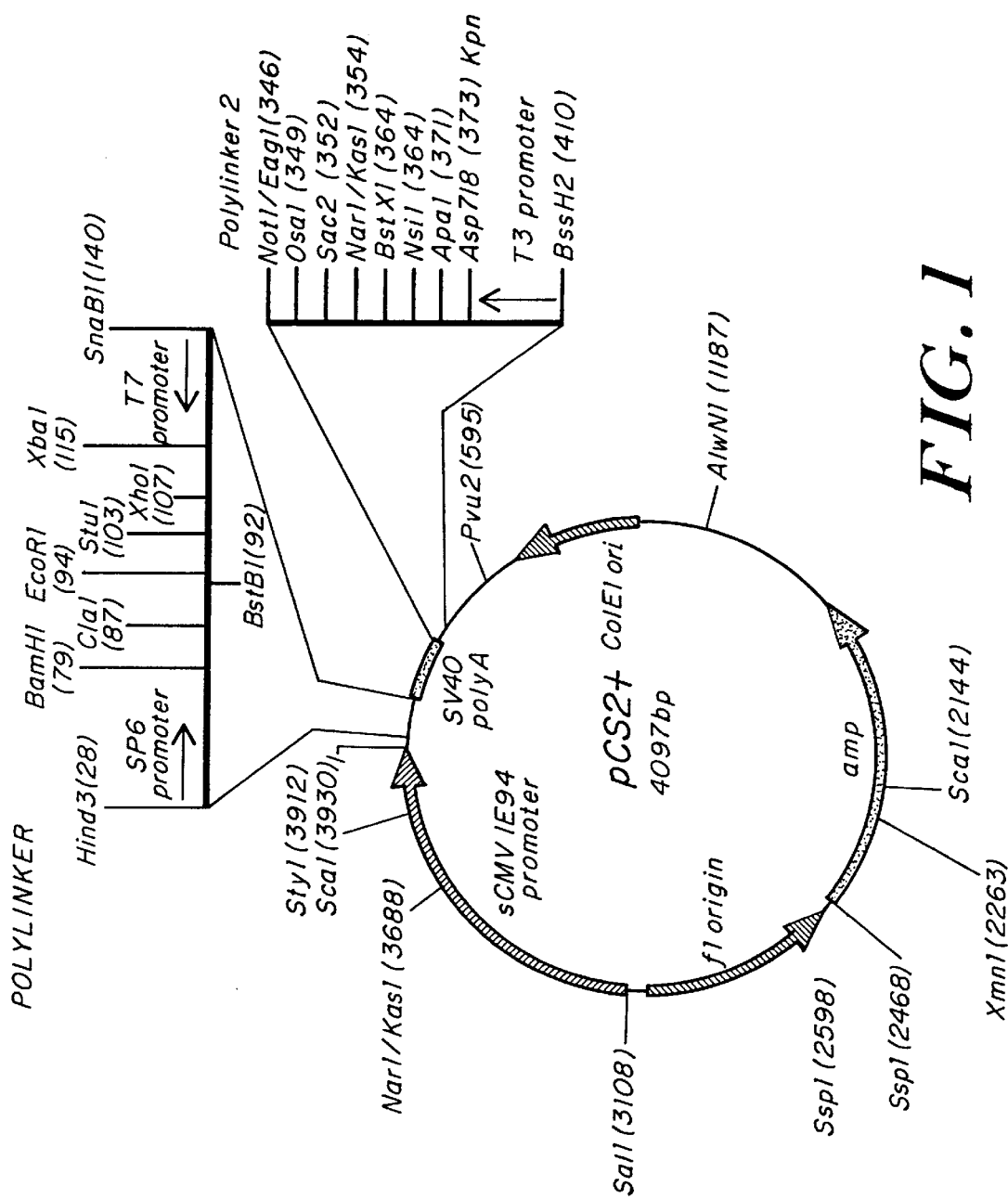
FIG. 1 illustrates the pCS2+ multi-purpose expression vector that can be used for in vivo expression by transfection/microinjection, or for in vitro RNA synthesis. The simian CMV IE94 promoter/enhancer drives high-level expression in most mammalian cell types, and is also expressed in a broad range of species, including Xenopus and zebrafish. An SP6 promoter has been introduce into the 5' untranslated region of the IE94 mRNA, and can be used to make RNA in vitro. A 27 nucleotide untranslated 5' leader (partially derived from the Xenopus β-globin mRNA 5' end) is present between the SP6 promoter and the polylinker. This leader provides a spacer on SP6 mRNAs before SP64/65 when injected into Xenopus embryos. A T7 promoter is present after the polylinker for synthesizing probes in the antisense direction. The SV40 late polyadenylation site is present after the polylinker/T7 promoter (originally a BamHI) to DraI fragment; this fragment is known to function in mammalian cells as well as Xenopus embryos). After the SV40 late poly-adenylation site are several restriction sites for linearizing the vector for RNA synthesis with the SP6 promoter. A T3 promoter is present in the same orientation as the T7 promoter after these sites. pCS2+ also contains an F1 origin for making single-stranded DNA. CS2+ contains the backbone of pBluescript II KS+, and rescues the lower strand of the polylinker shown above, so the SP6 primer should be used to sequence single-stranded DNA.

In principle, induction means any process in which the developmental pathway of one cell population is controlled by signals emitted from another. For instance, embryonic inductive signals are key regulatory proteins that function in vertebrate pattern formation, and are present in important signaling centers known to operate embryonically to define the organization of the vertebrate embryo. For example, these signaling structures include the notochord, a transient structure which initiates the formation of the nervous system and helps to define the different types of neurons within it. The notochord also regulates mesodermal patterning along the body axis. Another distinct group of cells having apparent signaling activity is the floorplate of the neural tube (the precursor of the spinal cord and brain) which also signals the differentiation of different nerve cell types. It is also generally believed that the region of mesoderm at the bottom of the buds which form the limbs (called the "Zone of Polarizing Activity" or "ZPA") operates as a signaling center by secreting a morphogen which ultimately produces the correct patterning of the developing limbs. Moreover, inductive signals are required for cell differentiation and morphogenesis throughout vertebrate development. Thus, in addition to initiating differences between cells in early development, inductive signals are also involved in formation and maintenance of most, if not all, adult organs and tissues.

The present invention concerns a novel paracrine signaling assay in which a "responsive" tissue (also referred to herein as a "target" tissue) is grafted onto an oocyte, or early stage embryo, which expresses exogenous proteins. Using the subject assay, it is possible to cause the oocyte to ectopically express secreted proteins, e.g. recombinant proteins, and then score for the effect of that protein on the grafted tissue, such as by detecting gene expression in the graft which is dependent on expression of the recombinant proteins by the oocyte. The subject assay will permit the identification of a variety of protein factors which are themselves active as inducing agents, or which act to antagonize an inducing agent, or which act to modify the response of the target tissue to an inducing agent. For instance, the subject assay can be employed to identify a vast number of protein factors which are regulators of cell proliferation, differentiation, or various other cell functions.

Thus, the present invention provides a method for cloning genes involved in, for example, hormone production (e.g., by pituitary or ovarian tissue), hematopoietic differentiation (e.g., generation of erythroid, lymphoid or myeloid tissue), neural cell differentiation and/or survival, regulation of the mitotic cell-cycle (e.g., control of cell proliferation) or meiotic cell-cycle (e.g., of oogenesis or spermatogenesis), induction of epithelial/mesodermal structures (e.g., in development of urogenital structures, limbs, or ocular tissue) or endodermal/mesodermal structures (e.g. of myocardial tissue such as cardiac muscle). Such factors identified through use of the present assay may have an ultimate end-use as a therapeutic agent, such as in wound-healing (e.g., by enhancing dermal growth); for treating connective tissue/skeletal disorders (e.g. in repair of cartilage and/or bone); for inhibiting tumor cell growth by inhibiting cell proliferation or causing differentiation of tumor cells; or as birth control agents.

In an illustrative embodiment, a protein factor cloned in the subject assay based on its ability to induce neuralization may be useful in the treatment of neurodegenerative disorders such as to facilitate control of adult neurons with regard to maintenance, functional performance, and aging of normal cells; repair and regeneration processes in chemically or mechanically lesioned cells; and prevention of degeneration and death which result from loss of differentiation in certain pathological conditions. In light of this understanding, the present invention specifically contemplates applications of the subject method to the identification of protein factors for use in the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease;

(iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

Inductive factors identified in the subject assay can also find use in cell culture, such as the in vitro generation of artificial organs by tissue culture techniques. For instance, factors which influence chondrogenesis, e.g. induce formation of chondroblasts, can be used in chondrocyte cultures to promote production of cartilage matrix. Likewise, lens-inducing factors can be identified in the subject assay, and subsequently used to culture presumptive lens ectoderm and produce lens tissue, or to repair damaged lens ex vivo.

Furthermore, the present invention contemplates the use of the subject assay to identify inductive factors which can be used in cell culture to induce or maintain neuronal differentiation of cultured neuronal cells. In an illustrative embodiment, the treated cells can be maintained in culture and used to provide in vitro assay systems. In another embodiment, the treated cells can be used as a source of tissue for transplantation in vivo. Intracerebral grafting has emerged as an additional approach to central nervous system therapies. For example, fetal neurons from a variety of brain regions can be successfully incorporated into the adult brain, and such grafts can alleviate behavioral defects. In the development of cell cultures for implantation, the use of a neuronal-inducing agents can prevent loss of differentiation, or where fetal tissue is used, especially neuronal stem cells, to enhance differentiation.

Other features of the subject assay include the ability to score for synergism, e.g. the ability of an inductive protein to synergize with other factors and produce a biological response in the target tissue that is different than the response of the tissue to that factor alone. For instance, inductive factors which synergize with noggin, Wnt or hedgehog can be identified. The subject assay can also be used to screen for protein factors able to modify the response of the target tissue to another inductive agent, e.g. the ability to alter the sensitivity of the responding tissue or to alter the phenotypic induction. Moreover, control of protein expression levels of the recombinant genes can facilitate detection of morphogenic characteristics of an inductive protein. Additionally, as the stage of development of the responding tissue can be readily manipulated at the time of grafting to the oocyte, the assay also allows an examination of temporal aspects of the inductive signal.

In general, the subject assay comprises a genetically modified oocyte, or early stage embryo (e.g. morulae stage or blastula stage), which express a recombinant protein(s). Grafted to the oocyte is a portion of a target tissue for which inductive agents are sought. In certain embodiments, the target tissue is also genetically modified with, for example, reporter gene constructs or recombinant receptor molecules. The ability of a recombinant protein produced by the oocyte to induce a biological response in the target tissue, or to antagonize an inductive pathway in those embodiments where such inhibitors are sought, can be readily determined by analysis of the target tissue. Examples of detection methods which can be employed to determine the effect of recombinant proteins on the target tissue include, but are not limited to: visual inspection of the morphology of the target tissue; detection of tissue-specific cell surface markers (e.g. by immunofluorescent staining); in situ hybridization assays to detect expression of tissue-specfic genes; and alteration of expression of a reporter gene construct provided in the target tissue.

In illustrative embodiments of the subject assay, the signaling cell is an unfertilized oocytes. While the present invention contemplates the use of oocytes isolated from any non-human vertebrate organism, preferred embodiments of the assay feature amphibian oocytes, particularly oocytes which are approximately the same size, or larger, than oocytes which can be isolated from frog species of the genus Xenopus, e.g. *Xenopus laevis*. In general, the larger oocytes are preferred for ease of mechanical manipulation, especially with respect to grafting of the target tissue (e.g. such eggs may tolerate larger grafts). Furthermore, expression of recombinant proteins and cell culturing techniques are each better characterized for amphibian oocytes, and a greater diversity of expression vectors are available for these systems. It will also be appreciated that the choice of oocyte platform for the subject assay can also depend on the source of the target tissue, particularly with respect to temperature and/or nutrient requirements. For instance, in order to graft mammalian tissue to the oocyte, the oocyte should be chosen so as to be viable when cultured at 34°–37° C. and in culture medium able to support the target tissue. In preferred embodiments, the oocyte is isolated from a frog or salamander; e.g. the oocyte is a Xenopus oocyte, such as from *Xenopus laevis* or *Xenopus Tropacalis*; e.g. the oocyte is a Rana oocyte, such as from *Rana esculenta* or *Rana pipiens*; e.g. the oocyte is a Notophthalmus oocyte, such as from *Notophthalmus vividescens*; e.g. the oocyte is a Pleurodeles oocyte, such as from *Pleurodeles waltlii*; e.g. the oocyte is a Cynops oocyte, such as from *Cynops pyrrhogaster*.

Isolation of amphibian oocytes is well known in the art (see, for example, Soreq et al. (1992) *Methods in Enzymology* 207:225–265; Wang et al. (1991) *Int J Biochem* 23:271–276; Sigel (1990) *J Membr Biol* 117:201–221; Martial et al. (1991) *Biochem Biophys Acta* 1090:86–90; Brockes (1992) *PNAS* 89:11386–11390; and U.S. Pat. Nos. 4,985,352, 5,288,621 and 5,202,257). For example, Xenopus oocytes can be harvested from female *Xenopus laevis* and processed using published techniques (Coleman et al., eds., *Transcription and Translation: A Practical Approach*. IRL Press, pp. 271–302; and Williams et al. (1988) *PNAS* 85:4939–4943). In one practice of the present invention, preparation of the assay includes obtaining oocytes from the excised ovaries of female frogs anesthetized by hypothermia and from which follicle cells have been removed by treatment with collagenase. Oocytes at a particular stage, e.g. Dumont stage V, can be selected and microinjected with the mRNA to be tested, e.g. in vitro transcribed RNA ("cRNA").

Isolation of other suitable oocytes can be, as a matter of course, carried out by one of ordinary skill in the art. For instance, techniques standardly used in generation of transgenic animals, such as protocols for inducing superovulation and isolating fertilized eggs from various mammals (e.g. mice, rabbits, rats, sheep, goats or pigs) can be slightly modified (i.e. no fertilization step) in order to allow for isolation of mammalian oocytes for use in the subject method (see, for example, U.S. Pat. No. 4,994,384). Moreover, protocols exist for in vitro maturation of mammalian oocytes, such as mature metaphase II oocytes.

Furthermore, the invention contemplates the use of early stage embryos in the assay, such as embryos in the morulae stage or blastula stage, in place of unfertilized oocytes. Such embryos can be isolated from pregnant animals following standard protocols known in the art, or alternatively, can be generated in culture by in vitro fertilization techniques. Use of such embryos in place of oocytes can be beneficial where the oocyte from that species is to small relative to the tissue explants to be used as targets. In one embodiment, mammalian blastula stage embryos (preferably non-human) are derived from fertilized eggs which have been transfected with an expression vector encoding the protein to be tested for inductive activity.

Several methods for expressing recombinant proteins in oocytes and embryos are generally known in the art. For example, expression of the recombinant protein(s) to be tested in the subject assay can be carried out by microinjection of cRNA encoding the protein, or by microinjection (or by other form of transfection) of an expression vector encoding the protein of interest. Either method can be carried out by employing the basics of expression cloning strategies known in the art. In one embodiment, cDNA libraries are cloned into vectors that can be used for in vitro RNA synthesis. For instance, the pCS2+/− vector utilized in the examples below contains SP6, T7 and T3 promoters that have been introduced upstream and downstream of the cloning site (see FIG. 1) in order to permit in vitro RNA synthesis upon linearization of the plasmid. In an illustrative embodiment, a plasmid containing the cDNA to be tested can be linearized by cutting downstream from the cDNA insert with a restriction enzyme. The post-restriction digest is digested with Proteinase K and then extracted with two phenol: chloroform (1:1) extractions. The resulting DNA fragments are then ethanol precipitated. The precipitated fragments are mixed with either T3 RNA polymerase (to make sense strand), or T7 RNA polymerase (to make anti-sense strand), plus rATP, rCTP, rGTP, rUTP, and RNase inhibitor. Simultaneously, capped RNA can be produced in vitro (Krieg and Melton, (1987) *Meth Enzymol* 155:397–415; and Richardson et al. (1988) *Bio/Technology* 6:565–570). Other exemplary vectors useful in the subject assay include: the pSP64T vector (Kreig et al. (1984) *Nuc Acid Res* 12:7057–7071) which contains the SP6 promoter and the 5' and 3' untranslated flanking regions of Xenopus β-globin cDNA to provide more stable RNA for translation in injectecd oocytes; the pOEV expression vector (Pfaff et al. (1990) *Anal Biochem* 188:192–199) which permits cloned DNA to be transcribed and translated directly in oocytes; and the pMT2 expression vector (Swick et al. (1992) *PNAS* 89:1812–1816).

The source of the gene(s) encoding the recombinant proteins to be tested as inducing agents is virtually unlimited. For example, xenopus oocytes are capable of expressing even plant genes. In one embodiment of the present invention, the recombinant gene is derived from a tissue or cell-type which is believed to affect the differentiation and/or growth of the responding tissue used in the assay. For example, cDNA libraries can be generated from an "inducing tissue", the library of genes then expressed in the oocyte of the present assay, and genes encoding the proteins which are active in the assay can be isolated. To illustrate, a size-fractionated cDNA library can be generated from poly (A)+ mRNA isolated from limb bud cells using standard protocols (See, for example, *Molecular Cloning A Laboratory Manual,* 2nd Ed., ed. by Sambrook, Fritsch and Maniatis (Cold Spring Harbor Laboratory Press:1989)) which has fractionated by size by centrifugation through a sucrose density gradient (Markovich et al. (1994) *J Biol Chem* 269:3022–3026; Steffgen et al. (1994) *Biochem J* 297:35–39; Su et al. (1992) *Mol Cell Biol* 12:5281–5287; and Perier et al. (1992) *J Neurochem* 59:1971–1974) and each cDNA pool then subcloned into, for example, pcDNAI or λPOP10 (Invitrogen, San Diego). The plasmid containing the cDNA can be purified, linearized, and transcribed to RNA, e.g. using the INVITROSCRIPT in vitro transcription system (Invitrogen). The cRNA is then microinjected into oocytes which are contacted with a target tissue for which an inducing molecule is sought, e.g. animal caps.

Where libraries of genes are to be tested, as in the above described size-fractionated library, each fraction can be tested individually, and those which yield positive results by the scoring criteria of the assay can then be further fractionated until the individual cloned gene(s) responsible for the activity are isolated. However, the present invention further provides a method for increasing the efficiency of isolating such clones. In one embodiment of the invention, rather than test each fraction individually, fractions are pooled and tested in an array format. For example, if 100 fractions are isolated, they can be pooled based on a 2-dimensional array (see FIG. 2), wherein, for example, fractions along each row and column are pooled to produce 20 sets of pooled fractions. Each pool is then tested, rather than each fraction, thereby reducing the number of assays from 100 to 20. Determining which fraction contains the gene interest when "hits" are detected in the subject assay can be provided by merely calculating the intersection of each column and row pool which scored postively. For instance, in the exemplary pooling of FIG. 2, hits in each of the row pools numbered 2, 6 and 10 and column pools 3 and 6 would mean that at least 3 of the 6 fractions numbered 23, 26, 53, 56, 93 and 96 contain genes which encode active inducers of the target tissues. Each of these fractions can be subsequently analyzed, and positive fractions can be further fractionated and tested until the gene is isolated. Moreover, the "SIP" assay can be extended beyond 2-dimensional arrays, e.g. to 3-D arrays.

To detect recombinant inductive proteins being produced by the oocyte, a number of techniques are available. For instance, visual inspection of the morphology of the target tissue can be used to determine iduction. To illustrate, the formation of neuritic process can be visualized under a light microscope, as can the general morphological features of other tissue types. Another method of scoring for induction is to by detecting tissue-specific cell surface markers (e.g. by immunofluorescent staining). Many such markers are known in the art, and antibodies are readily available. For example, the presence of chondroitin sulphate proteoglycans as well as type-II collagen are correlated with cartilage production in chondrocytes, and each can be detected by immunostaining. Similarly, the human kidney differentiation antigen gp160, human aminopeptidase A, is a marker for induction of kidney differentiation. In another embodiment, in situ hybridization assays are used to detect expression of tissue-specfic genes. In yet another embodiment, the alteration of expression of a reporter gene construct provided in the target tissue provides a means of detecting the induction of the target tissue. For example, reporter gene constructs derived using the transcriptional regulatory sequences, e.g. the promoters, for developmentally regulated genes can be used to drive the expression of a detectable marker, such as a luciferase gene. In an illustrative embodiment, the construct is derived using the promoter sequence from an early response gene such as gsc, Xlim-1, Xotz-2, XFKH1, Xnot, Xbra, Mix.1, which are genes activated in various tissues during gastrulation.

The choice of target tissue, like the choice of sources for genes to be screened, can also be quite large. Thus, the target tissue can be derived from, for example, embryonic or fetal tissues, from adult tissues (including tumors and other neoproliferative or hyperproliferative tissue samples), as well from cell culture.

This invention further contemplates a method of generating and screening sets of combinatorial mutants of known inductive proteins, as well as truncation mutants. The purpose of screening such combinatorial libraries is to generate, for example, homologs of an inductive protein which are active as one of either an agonists or an antagonist of the biological activity of the wild-type protein, or alternatively, which possess novel activities all together. To illustrate, homologs of basic Fibroblast Growth Factor (bFGF) can be engineered by the present method to provide more efficient binding to an FGF receptor, and still retain at least a portion of an activity associated with authentic bFGF. For example, combinatorially-derived homologs can be generated to have an increased potency relative to a naturally occurring bFGF. Likewise, homologs of an inductive protein can be generated by the present combinatorial approach to act as antagonists, in that they are able to bind a receptor for that protein, yet do not induce any biological response, thereby blocking the action of wild-type protein. Moreover, manipulation of certain domains of an inductive protein, such as activin, by screening mutational libraries through the present method can provide domains more suitable for use in fusion proteins, such as one that incorporates portions of other proteins which are derived from the extracellular matrix and/or which bind extracellular matrix components.

In one aspect of this method, the amino acid sequences for a population of inductive protein homologs or other related proteins are aligned, preferably to promote the highest homology possible. Such a population of variants can include, for example, homologs from one or more species, as well as various isoforms from one species. For instance, the family of bone morphogenic proteins (BMPs), as well as other members of the Transforming Growth Factor-β (TGFβs), can be used to generate a combinatorial library. To analyze the sequences of a population of related proteins, the amino acid sequences (or nucleotide sequences) of interest can be aligned relative to sequence homology. The presence or absence of amino acids from an aligned sequence of a particular variant is relative to a chosen consensus length of a reference sequence, which consensus length can be real or artificial. Analysis of the alignment of the proteins can give rise to the generation of a degenerate library of polypeptides comprising potential sequences based on conserved and non-conserved residues in each position of the aligned sequences. A combinatorial library can then be produced by way of a degenerate library of genes encoding a library of polypeptides which each include at least a portion of potential protein sequences. For instance, a mixture of synthetic oligonucleotides can be enzymatically ligated into gene sequences such that the degenerate set of potential sequences are expressible as individual polypeptides.

There are many ways by which the library can be generated from a degenerate oligonucleotide sequence. Chemical synthesis of a degenerate gene sequence can be carried out in an automatic DNA synthesizer, and the synthetic genes then be ligated into an appropriate expression vector for in vivo expression by transfection of the vector into the oocyte, or in vitro RNA synthesis of the library. The purpose of a degenerate set of genes is to provide, in one mixture, all of the sequences encoding the desired set of potential sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules,* ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249:404–406; Cwirla et al. (1990) *PNAS* 87:6378–6382; as well as U.S. Pat. Nos. 5,223,409, 5,198,346, and 5,096,815).

To detect an antagonist in the present assay, an authentic form of the protein can be co-expressed with the potential antagonist and the ability of target tissue to respond in the presence and absence of the potential antagonist can be assessed. In such embodiments, a reporter gene construct present in the target tissue can be quite useful for discerning small, yet significant, inhibition of the authentic inducers activity.

Moreover, it may be desirable to co-express a marker gene in the oocyte in order to standardize the comparison of effects based on level of expression occuring in the oocytes. For example, an α-amylase gene construct can be provided in the oocyte, and the amylase activity measured in the oocyte (Urnes et al. (1990) *Gene* 95:267–274. The level of expression for other proteins can therefore be standardized based on the amount of recombinant amylase produced. This construct can also be important in ascertaining the effect of a putative morphogen, such as activin, on the target tissue. Morphogens typically have sharp thresholds in their response for inducing different kinds of tissues/responses. Dose response curves can therefore be constructed based on the level of expression of the amylase reporter in the oocyte.

The method of the present invention will also facilitate further determination of a potential role of an inductive protein as a "morphogen", that is, a molecule whose tight threshold of concentration determines specific cell fate during development (Wolpert, L. (1969) *J Theor Biol.* 25:1–47). For instance, the subject assay system can be used for the identification, isolation, and study of genes and gene products that are expressed in response the presence of an inductive protein, and therefore likely involved in the biological response of the target tissue. These genes would be "downstream" of the inductive signal, and may be required, for example, for differentiation of the tissue. For instance, if new transcription is required for the neuralization of the target tissue, a subtractive cDNA library prepared with control tissue (no inductive agent) and target tissue grafted to an oocyte expressing the inducer, and can be used to isolate genes that are turned on or turned off by this process. The powerful subtractive library methodology incorporating PCR technology described by Wang and Brown is an example of a methodology useful in conjunction with the present invention to isolate such genes (Wang et al. (1991) *PNAS. USA* 88:11505–11509). For example, this approach has been used successfully to isolate more than sixteen genes involved in tail resorption with and without thyroid hormone treatment in Xenopus. A similar approach involves the use of the differential display and cloning methods, such as described in Liang et al. (1992) *Cancer Res* 52:6966–6998; Liang et al. (1992) *Science* 257:967–971; and Liang et al. (1993) *Nuc Acid Res* 21:3269–3275). Utilizing control and treated cells, the induced pool can be subtracted from the uninduced pool to isolate genes that are turned on, and then the uninduced pool subtracted from the induced pool for genes that are turned off. From this screen, it is expected that two classes of mRNAs can be identified. Class I RNAs would include those RNAs expressed in untreated cells and reduced or eliminated in induced cells, that is the down-regulated population of RNAs. Class II RNAs include RNAs that are upregulated in response to induction and thus more abundant in treated than in untreated cells. RNA extracted from treated vs untreated cells can be used as a primary test for the classification of the clones isolated from the libraries. Clones of each class can be further characterized by sequencing and, their spatiotemporal distribution determined in the embryo by in situ and developmental northern blots analysis.

For example, in one embodiment of this subtractive assay, special attention can be given to genes that prove to be an immediate early response to induction. To qualify as such, these genes should, in addition to having an appropriate expression pattern, fulfill the following three criteria. First, the RNA should appear quickly following contact with the oocyte expressing the inducer protein. To test this requirement, RNA can be isolated at different times from induced cells and scored for gene expression by northern blots. Second, the induction of the gene should not require previous protein synthesis. Thus, target tissue can be incubated with cycloheximide immediately prior to grafting to the oocyte. This strategy has been used, for example, to identify homeobox genes exhibiting an immediate early response (Rosa, F. M. (1989) *Cell.* 57:965–974). Third, where the inducer is provided as a soluble factor (i.e. diffusible morphagen) immediate early response genes should be expressed as a result of contact with inducer and not from a secondary cell-cell induction. One method to differentiate between these two responses is to dissociate the target tissue from the oocyte by providing a permeable membrane between the two (e.g. indirect grafting of the tissue to the oocyte), such as a porous gel, and comparing the amount of the induced transcript in dissociated tissue versus directly grafted tissue. If the levels are comparable in both types of systems, then it may be concluded that cell-cell contact was not required for this induction and it is thus likely a direct response of inducer.

Moreover, the subject assay system further provides for the cloning of receptor molecules for binding of a known inducer. In such embodiments, the known inducer can be expressed in the oocyte, and gene libraries screened by expression in the target tissue.

The invention, now being generally described, will be more readily understood by reference to the following examples, which are included merely for purposes of illustration of certain aspects and embodiments of the present invention and are not intended to limit the invention.

EXEMPLIFICATION

The major obstacle to identifying neural-inducing factors is the lack of a suitable assay for neural induction. Although no assay that can be used to specifically identify neural inducers is currently available, two assays have been developed that could in principle be used for this purpose. In the "neuralization assay", gastrula stage ectoderm is explanted, treated with a test factor or conditioned media and then assayed for neural marker expression. In the "axial rescue" assay, which was used to clone the noggin gene, an RNA is injected into a ventralized egg. If the protein encoded by that RNA induces dorsal mesoderm formation, then dorsal structures are formed in the ventralized egg. Thus noggin was first identified by virtue of its ability to induce dorsal mesoderm in ventralized eggs; it was only later that it was found to possess neural-inducing properties as well.

The subject paracrine assay, in its operation, effectively combines elements of both the "neuraliztion" and "axial rescue" assays. In the embodiments detailed in the examples below, the assay includes a responding tissue (e.g. presumptive ectoderm) that is competent to form neural tissue if it receives the appropriate signal, and it has a signaling tissue (e.g. oocyte) in which it is possible to express exogenous proteins by RNA injection. With this type of two-component system, it should be possible to use a SIP selection procedure to identify proteins that, when expressed ectopically in the signaling tissue, cause neural induction in the responding tissue.

The strategy of the screens described below was to graft a gastrula stage animal cap onto an oocyte that had been injected with mRNA synthesized in vitro from pools of a Xenopus cDNA library. After several days in culture the animal cap graft is removed and analyzed by RT-PCR for the expression of neural markers for different regions of the nervous system. For instance, six neural genes can be analyzed: NCAM (pan-neural), opsin (for eye), engrailed-2 (for mid brain), krox-20 (for hind brain), Xlhbox6 (for spinal cord) and tanabin (for spinal cord). If a cDNA pool encodes a protein that induces any of these neural markers, the pool will be further subdivided and the process repeated until a single clone is isolated. Unlike the "axial rescue" assay, the subject assay can distinguish between extracellular and intracellular effects of a putative inducer, and between direct neural induction and indirect neural induction that occurs as a secondary consequence of mesoderm induction.

We have generated five cDNA libraries from tissues that would be expected to express secreted factors with neural-inducing activities. Four libraries were constructed in a frog expression plasmid (pCS2+) that was designed for maximal expression of exogenous genes in Xenopus oocytes. One of these libraries was constructed from poly(A)+ RNA isolated from the notochord, which underlies the neural tube is a primary source of secreted neural-inducing signals in the vertebrate embryo. Two of the cDNA libraries were constructed from poly(A)$^+$ RNA isolated from Xenopus embryos at the gastrula or early neurula stages of development, when neural induction and patterning occur. Since dorsal mesoderm is believed to be a source of neural-inducing signals, we have also constructed a cDNA library using poly(A)+ RNA isolated from embryos hyperdorsalized by LiCl treatment. Finally, we have obtained a Xenopus cDNA expression library that was made from RNA isolated from early gastrula organizer (Spemann's organizer) explants, another primary source of neural-inducing signals.

Additionally, it may be desirable to verify that any neural induction observed in the animal cap is not in fact due to the induction of mesoderm of the target tissue, which could in turn release secreted factors that induce neural tissue in neighboring cells. Likewise, it will be necessary to demonstrate that neural induction is not a result of the synthesis and secretion of noggin in the animal cap. Noggin made in this way could induce neural tissue in the animal cap by autocrine and paracrine signaling. Thus, in addition to the six neural markers described above, it may be desirable to also determine the level of noggin, muscle actin (a muscle marker), goosecoid (a dorsal mesoderm marker) and brachyury (a panmesodermal marker) in the animal cap sample. For instance, RT-PCR procedures can be used to rapidly and simultaneously measure levels of all ten genes in a single tissue sample.

Furthermore, several approaches can be used to reduce the likelihood of cloning previously characterized proteins, such as FGF, activin and noggin, that are expected to be present in the cDNA libraries. One approach will be to use gastrula animal caps which, in contrast to blastula animal caps, have lost the ability to form mesoderm in response to FGF and activin. Another will be to use animal caps explanted from embryos that have been injected with a dominant negative FGF receptor, which inhibits both FGF and activin signaling. If RNA synthesized in vitro from a cDNA pool leads to neural induction (without mesoderm induction), PCR will be used to determine whether the cDNA pool contains noggin. If necessary, the noggin gene can be eliminated from the RNA pool by adding an excess of noggin anti-sense RNA and digesting with RNase H. This same strategy also could be used to eliminate other previously identified inducers, such as members of the FGF and activin families, from an RNA or cDNA pool.

It will be apparent from the present disclosure that a variety of proteins can be identified by this screen. By assaying for the expression of a variety of neural genes in each tissue sample, it may be possible to identify and discern between secreted proteins that have general neural-inducing activity versus those that induce specific regions of the nervous system. Although the primary reason for assaying mesodermal genes is to exclude the possibility that any observed neural induction is indirect, it may also be possible to identify novel genes that have mesoderm-inducing activity. Similarly, it may be possible to identify secreted proteins that induce noggin synthesis in animal cap cells.

Moreover, noggin does not induce the expression of molecular markers for the mid-brain, hind-brain or spinal cord, suggesting that other factors act together with noggin, either synergistically or as modifiers of noggin induction, to induce these regions of the nervous system. Of the six neural marker genes that we have measured by RT-PCR, only NCAM is reproducibly induced by the expression of noggin in the oocyte. By expressing noggin RNA together with synthetic library RNA and assaying for the expression of all six neural genes, we may be able to identify factors that act together with noggin to specify other regions of the nervous system.

Preparation of cRNA.

Eggs from the South African clawed frog *Xenopus laevis* were fertilized and cultured in vitro. At the gastrula and neurula stages of development, the vitelline membrane was removed, total cellular RNA was isolated by the guanidine isothiocyanate method (e.g. Chomczynski method described in U.S. Pat. No. 4,843,155), and poly(A)+ RNA was selected using oligo-dT. A directional cDNA library was constructed in pCS2 as previously described (). pCS2 is a derivative of p in which a 25 base pair region of the 5' untranslated region of the *Xenopus laevis* globin gene is inserted just upstream of the polylinker. Templates for in vitro transcription were prepared by linearizing plasmid DNA isolated from library pools with NotI. cRNA transcripts were synthesized in vitro using SP6 RNA polymerase as previously described().

Isolation and Injection of Oocytes.

*Xenopus laevis* oocytes were surgically isolated and manually defolliculated. Defolliculated oocytes were incubated at 18° C. in 1X Normal Amphibian Medium (NAM: 7.5 mM Tris, pH 7.6; 88 mM NaCl 1 mM KCl; 2.4 mM NaHCO$_3$; 8.2 mM MgsO$_4$; 0.33 mM Ca(N0$_3$)$_2$; 0.4 mM CaCl$_2$ gentamycin). Defolliculated oocytes were injected with 50 nl library cRNA transcripts (approximately 1 $\mu$g/$\mu$l) or between 0.5–50 ng of cRNA transcripts encoding the secreted factors noggin, activin or fibroblast growth factor (FGF). Injected oocytes were incubated for 24 hours at 18°–20° C. in 1X (NAM) containing gentamycin.

Grafting of Tissue Explants onto Oocytes.

*Xenopus laevis* eggs were fertilized and cultured in vitro. At various stages of development, the vitelline membrane was removed and the animal cap (presumptive ectoderm) was explanted from the embryo. The explant was placed in direct contact with a manually defolliculated *Xenopus laevis* oocyte that had been injected 24 hours previously with library cRNA or cRNA encoding noggin, activin or FGF.

Assessment of the Effect of the Recombinant Proteins.

After the explant-oocyte recombinant was cultured for 2 days at 18° C., the embryonic tissue was removed from the oocyte and reverse transcriptase-polymerase chain reaction (RT-PCR) was used to measure the expression levels of various neural and mesodermal marker genes. Alternatively, the recombinant was fixed and stained for marker gene expression by in situ hybridization or by immunostaining.

In one embodiment of the present invention, the induction assay involves the grafting of ectoderm, the embryonic tissue that is competent to form mesoderm or nervous tissue during normal embryonic development, onto oocytes injected with synthetic RNA. The hypothesis is that if the RNA injected into oocyte encodes a secreted mesoderm inducer, then the grafted ectoderm will differentiate into mesoderm. Likewise, if the RNA injected into the oocyte encodes a secreted neural inducer, then the grafted ectoderm will form neural tissue. To test this hypothesis, we have injected RNA encoding activin, a mesoderm inducer, or RNA encoding noggin, a neural inducer, into the oocyte and then assayed for the expression of various mesodermal and neural markers in the grafted animal cap.

Use of Activin to Assess the Specificity and Sensitivity of the Paracrine Assay

Blastula stage animal caps (presumptive ectoderm) were grafted onto oocytes injected with mRNA encoding activinB, a secreted member of the TGF-$\beta$ family of growth factors. The grafted animal caps exhibited a similar phenotype as ungrafted animal caps that had been treated with purified activin; over 2–3 days, the tissue elongated and differentiated into mesoderm or mesodermal derivatives such as muscle, cement gland, melanocytes and eyes. Injection of as little as 100 femtograms of activin RNA into the oocyte was sufficient to induce morphological extension and cement gland formation in the animal cap graft. A close association between the animal cap and the oocyte was required to manifest these effects; animal caps placed~1 cm from the oocyte/animal cap graft did not extend or form mesodermal derivatives.

These results do not rule out the possibility that the synthesis of activin in the oocyte leads to the release of another secreted factor that then acts upon the grafted animal caps. A dominant negative fibroblast growth factor (FGF) receptor, in addition to inhibiting FGF signaling (Amaya et al. (1991) *Cell* 66:257–270), also inhibits most aspects of activin signaling in the Xenopus embryo. Expression of the dominant negative FGF receptor in the animal cap (prior to grafting it onto the oocyte) substantially reduced the amount of morphological extension and cement gland formation induced by activin-expressing oocytes.

The effects of activin did not appear to be due to the stimulation of FGF release from the oocyte since animal caps grafted onto FGF-expressing oocytes exhibited a different phenotype than animal caps grafted onto activin-injected oocytes; they elongated and formed muscle but did not form cement gland, melanocytes or eyes. Taken together, these findings suggest that the injection of activin RNA into the oocyte leads to the synthesis and release of activin protein, which then acts in a paracrine manner to cause induction in the grafted animal cap.

Paracrine Signaling by the Secreted Protein Noggin

The secreted protein noggin may be one of the neural-inducing signals released amphibian dorsal mesoderm. Noggin mRNA is expressed in the organizer and subsequently in the notochord, a primary source of neural-inducing factors located directly beneath the ectoderm. In addition, purified noggin protein induces the expression of anterior neural markers in Xenopus ectoderm explanted at the gastrula stage of development, the time of endogenous neural induction.

To determine whether the paracrine system can be used to assay neural induction, Xenopus animal caps were grafted onto oocytes expressing noggin and then analyzed for expression of mesodermal and neural marker genes. Animal caps were explanted either before or after the mid-blastula transition (Nieuwkoop/Faber stage 8.5), the time point in early development when zygotic transcription commences and cleavage synchrony is lost. In animal caps explanted from either pre-MBT (N/F stage 7-8) or post-MBT (NF stage 9-10 embryos, noggin expression in the oocyte led to pronounced morphological extension, the formation of cement gland and the induction of the neural marker NCAM. These effects did not appear to be due to a secondary consequence of mesoderm induction since in most experiments noggin did not induce expression of muscle actin, a gene that is expressed in muscle, a mesoderm derivative.

These results suggest that it is possible to use the paracrine assay to express secreted proteins that specify neural tissue. This capability should make it possible to identify novel secreted proteins that have neural-inducing properties (see below).

Paracrine Signaling by the Cell-Surface Protein Wnt

Members of the Wnt family of secreted glycoproteins may also be involved in the specification of cell fate in the vertebrate nervous system. The Wnt-1 protein is expressed in the brain and spinal cord of the mouse and is required for the development of certain regions of the central nervous system; mice in which the Wnt-1 gene has been deleted exhibit severely abnormal development of the midbrain and cerebellum, and generally die soon after birth. Twelve different members of the Wnt protein family are expressed in Xenopus, three of which are localized to the central nervous system. XWnt-1, XWnt-3a and XWnt-5a are expressed in different regions of the brain and spinal cord during gastrula and neurula stages of Xenopus development, but their role in nervous system development has not yet been defined.

Information concerning the mode of action of Wnt proteins have come almost exclusively from analyses of wingless, the Drosophila homolog of Wnt. In Drosophila, genetic and biochemical evidence suggests that wingless is a secreted protein that is restricted in its activity to cells that are less than several cell diameters away. This short range of action has been attributed to the poor solubility of the wingless protein; to date, the wingless and Wnt proteins have not yet been isolated in active soluble, form.

To determine whether the subject assay can be used to study Wnt signaling, Xenopus animal caps were grafted onto oocytes that had been injected with mouse Wnt-1 RNA, and then assayed for the expression of mesodermal and neural genes. The results suggest that the competence of presumptive ectoderm to respond to Wnt-1 is modified at or soon after the mid-blastula transition (MBT), when zygotic transcription commences. In pre-MBT animal caps, Wnt-1 induced the expression of muscle actin, a mesodermal gene marker, but had no effect on the level of the neural marker NCAM. In post-MBT animal caps, Wnt-1 had no effect on muscle actin or NCAM expression.

These results suggest that the Xenopus oocyte can be used as a way to present the otherwise insoluble Wnt ligand to animal cap cells that express the putative Wnt receptor and its associated signaling molecules. Thus biochemical and molecular genetic approaches can now be used to identify elements of the Wnt signaling pathway.

All of the above-cited references and publications are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for identifying an extracellular signal protein which induces a change in at least one of growth or differentiation of a cell, comprising (i) contacting a isolated responsive signaling tissue with a tissue, said signaling tissue selected from a group consisting of a genetically modified non-human oocyte expressing a recombinant protein and a genetically modified early stage non-human embryo expressing a recombinant protein, which isolated responsive and signaling tissues are exogenous to each other and (ii) detecting a change in growth or differentiation of cells of said isolated responsive tissue, wherein a change in growth or differentiation of said isolated responsive tissue in the presence of said recombinant protein relative to growth or differentiation of said isolated responsive tissue in the absence of said recombinant protein is indicative of an inductive activity of said recombinant protein.

2. The method of claim 1, wherein changes in said isolated responsive tissue are detected by a method selected from a group consisting of (i) visual inspection of the morphology of said isolated responsive tissue; (ii) detection of tissue-specific cell surface markers on said target tissue; (iii) in situ hybridization assays to detect expression of tissue-specfic genes by said isolated responsive tissue; and (iv) alteration of expression of a reporter gene construct provided in said isolated responsive tissue.

3. The method of claim 1, wherein said recombinant protein is produced by exogenous RNA microinjected into said signaling tissue.

4. The method of claim 1, wherein said recombinant protein is produced by a recombinant gene construct expressed by said signaling tissue.

5. The method of claim 1, wherein said isolated responsive tissue is embryonic tissue.

6. The method of claim 5, wherein said embryonic tissue is competent to form neuronal tissue.

7. A method for cloning a gene encoding an extracellular signal protein which is an inducer of growth or differentiation of a cell, comprising:

(i) contacting a isolated responsive tissue with a signaling tissue, said signaling tissue selected from a group consisting of a genetically modified non-human oocyte expressing a variegated library of recombinant proteins and a genetically modified early stage non-human embryo expressing a variegated library of recombinant proteins which isolated responsive and and signaling tissues are exogenous to each other;

(ii) detecting a change in growth or differentiation of cells of said isolated responsive tissue, wherein a change in growth or differentiation of said isolated responsive tissue in the presence of said recombinant protein library relative to growth or differentiation of said isolated responsive tissue in the absence of said recombinant proteins is indicative of an inductive activity of at least said recombinant protein; and (iii) isolating the gene encoding the protein of said variegated library of recombinant proteins which induces the change in said target tissue.

8. An assay system comprising (i) an isolated responsive tissue grafted to (ii) a genetically modified non-human oocyte expressing a recombinant protein.

* * * * *